United States Patent
Donnelly et al.

(10) Patent No.: US 10,492,821 B2
(45) Date of Patent: Dec. 3, 2019

(54) SELECTIVE TISSUE REMOVAL TREATMENT DEVICE

(71) Applicant: HydroCision, Inc., Billerica, MA (US)

(72) Inventors: Howard W. Donnelly, Needham, MA (US); Mark Lewis, Haverhill, MA (US); Lynne Messina, Cambridge, MA (US)

(73) Assignee: HYDROCISION, INC., North Billerica, MA (US)

( * ) Notice: Subject to any disclaimer, the term of this patent is extended or adjusted under 35 U.S.C. 154(b) by 0 days.

(21) Appl. No.: 15/937,415

(22) Filed: Mar. 27, 2018

(65) Prior Publication Data

US 2018/0214172 A1    Aug. 2, 2018

Related U.S. Application Data

(63) Continuation-in-part of application No. 15/631,722, filed on Jun. 23, 2017.

(60) Provisional application No. 62/354,515, filed on Jun. 24, 2016.

(51) Int. Cl.
| | |
|---|---|
| A61B 17/3203 | (2006.01) |
| A61B 8/08 | (2006.01) |
| A61B 8/12 | (2006.01) |
| A61B 17/00 | (2006.01) |
| A61B 90/00 | (2016.01) |

(52) U.S. Cl.
CPC .......... *A61B 17/3203* (2013.01); *A61B 8/085* (2013.01); *A61B 8/12* (2013.01); *A61B 8/08* (2013.01); *A61B 2017/00199* (2013.01); *A61B 2090/378* (2016.02); *A61B 2217/005* (2013.01)

(58) Field of Classification Search
CPC .......... A61B 17/3203; A61B 2217/005; A61B 8/085; A61B 17/320092; A61B 17/320016; A61B 17/00234
See application file for complete search history.

(56) References Cited

U.S. PATENT DOCUMENTS

| | | |
|---|---|---|
| 1,889,425 A | 11/1932 | Sorensen |
| 1,902,418 A | 3/1933 | Pilgrim |
| 3,565,062 A | 2/1971 | Kuris |
| 3,590,813 A | 7/1971 | Roszyk |
| 3,818,913 A | 6/1974 | Wallach |

(Continued)

FOREIGN PATENT DOCUMENTS

| | | |
|---|---|---|
| DE | 4018736 A1 | 1/1992 |
| EP | 0551920 A1 | 7/1993 |

(Continued)

OTHER PUBLICATIONS

International Search Report and Written Opinion for Application No. PCT/US2017/039046, dated Sep. 26, 2017. 7 pages.

(Continued)

*Primary Examiner* — Emily L Schmidt
*Assistant Examiner* — Tiffany Legette
(74) *Attorney, Agent, or Firm* — Bochner IP; Andrew D. Bochner

(57) ABSTRACT

This disclosure describes techniques and devices for improvement of surgical outcomes for tissue removal surgeries. A surgical instrument with adjustable and selective resection is described. The disclosed devices and methods allow selective tissue removal.

12 Claims, 12 Drawing Sheets

(56) References Cited

U.S. PATENT DOCUMENTS

| | | |
|---|---|---|
| 3,930,505 A | 1/1976 | Wallach |
| 3,965,901 A | 6/1976 | Penny et al. |
| 4,024,866 A | 5/1977 | Wallach |
| 4,111,490 A | 9/1978 | Liesveld |
| 4,137,804 A | 2/1979 | Gerber et al. |
| 4,282,867 A | 8/1981 | Du Toit |
| 4,368,734 A | 1/1983 | Banko |
| 4,435,902 A | 3/1984 | Mercer et al. |
| 4,560,373 A | 12/1985 | Sugino et al. |
| 4,690,672 A | 9/1987 | Veltrup |
| 4,694,828 A | 9/1987 | Eichenbaum |
| 4,705,500 A | 11/1987 | Reimels et al. |
| 4,715,848 A | 12/1987 | Beroza |
| 4,898,574 A | 2/1990 | Uchiyama et al. |
| 4,913,698 A | 4/1990 | Ito et al. |
| 4,935,006 A | 6/1990 | Hasson |
| 5,027,792 A | 7/1991 | Meyer |
| 5,037,431 A | 8/1991 | Summers et al. |
| 5,057,098 A | 10/1991 | Zelman |
| 5,135,482 A | 8/1992 | Neracher |
| 5,135,484 A | 8/1992 | Wright |
| 5,186,714 A | 2/1993 | Boudreault et al. |
| 5,195,958 A | 3/1993 | Phillips |
| 5,217,465 A | 6/1993 | Steppe |
| 5,230,704 A | 7/1993 | Moberg et al. |
| 5,242,449 A | 9/1993 | Zaleski |
| 5,250,065 A | 10/1993 | Clement et al. |
| 5,255,017 A | 10/1993 | Lam |
| 5,259,842 A | 11/1993 | Plechinger et al. |
| 5,300,022 A | 4/1994 | Klapper et al. |
| 5,318,518 A | 6/1994 | Plechinger et al. |
| 5,322,504 A | 6/1994 | Doherty et al. |
| 5,370,609 A | 12/1994 | Drasler et al. |
| 5,453,088 A | 9/1995 | Boudewijn et al. |
| 5,476,450 A | 12/1995 | Ruggio |
| 5,496,267 A | 3/1996 | Drasler et al. |
| 5,505,729 A | 4/1996 | Rau |
| 5,527,330 A | 6/1996 | Tovey |
| 5,551,448 A | 9/1996 | Matula et al. |
| 5,556,406 A | 9/1996 | Gordon et al. |
| 5,562,640 A | 10/1996 | McCabe et al. |
| 5,562,692 A | 10/1996 | Bair |
| 5,591,184 A | 1/1997 | McDonnell et al. |
| 5,607,391 A | 3/1997 | Klinger et al. |
| 5,620,414 A * | 4/1997 | Campbell, Jr. ..... A61B 17/3203 604/150 |
| 5,667,480 A | 9/1997 | Knight et al. |
| 5,674,226 A | 10/1997 | Doherty et al. |
| 5,713,849 A | 2/1998 | Bosma et al. |
| 5,713,851 A | 2/1998 | Boudewijn et al. |
| 5,766,194 A | 6/1998 | Smith |
| 5,782,795 A | 7/1998 | Bays |
| 5,788,667 A | 8/1998 | Stoller |
| 5,853,384 A | 12/1998 | Bair |
| 5,871,462 A | 2/1999 | Yoder et al. |
| 5,908,403 A | 6/1999 | Bosma et al. |
| 5,944,686 A | 8/1999 | Patterson et al. |
| 5,947,988 A | 9/1999 | Smith |
| 6,066,150 A | 5/2000 | Gonon |
| 6,135,977 A | 10/2000 | Drasler et al. |
| 6,216,573 B1 | 4/2001 | Moutafis et al. |
| 6,280,302 B1 | 8/2001 | Hashish et al. |
| 6,322,533 B1 | 11/2001 | Gonon |
| 6,375,635 B1 | 4/2002 | Moutafis et al. |
| 6,402,715 B2 | 6/2002 | Manhes |
| 6,451,017 B1 | 9/2002 | Moutafis et al. |
| 6,511,493 B1 | 1/2003 | Moutafis et al. |
| 6,669,710 B2 | 12/2003 | Moutafis et al. |
| 6,960,182 B2 | 11/2005 | Moutafis et al. |
| 7,122,017 B2 | 10/2006 | Moutafis et al. |
| 7,337,538 B2 | 3/2008 | Moutafis et al. |
| 7,431,711 B2 | 10/2008 | Moutafis et al. |
| 7,717,685 B2 | 5/2010 | Moutafis et al. |
| 8,062,246 B2 | 11/2011 | Moutafis et al. |
| 8,162,966 B2 | 4/2012 | Connor et al. |
| 8,574,186 B2 | 11/2013 | Fischer |
| 9,597,107 B2 | 3/2017 | Staid et al. |
| 2002/0050197 A1 | 5/2002 | Moutafis et al. |
| 2002/0111579 A1* | 8/2002 | Moutafis ............ A61B 17/3203 604/43 |
| 2002/0176788 A1 | 11/2002 | Moutafis et al. |
| 2004/0243157 A1 | 12/2004 | Connor et al. |
| 2006/0129086 A1 | 6/2006 | McRury et al. |
| 2006/0229550 A1 | 10/2006 | Staid et al. |
| 2006/0264808 A1 | 11/2006 | Staid et al. |
| 2007/0239085 A1* | 10/2007 | Fehre ............... A61B 17/22004 601/4 |
| 2009/0306692 A1 | 12/2009 | Barrington et al. |
| 2010/0010524 A1 | 1/2010 | Barrington et al. |
| 2010/0331883 A1* | 12/2010 | Schmitz ............ A61B 10/0275 606/249 |
| 2017/0312282 A1* | 11/2017 | Robinson ............ A61K 9/0019 |
| 2017/0367724 A1 | 12/2017 | Donnelly et al. |

FOREIGN PATENT DOCUMENTS

| | | |
|---|---|---|
| WO | 1990/05493 A1 | 5/1990 |
| WO | 1996/24299 A1 | 8/1996 |
| WO | 1999/33510 A1 | 7/1999 |

OTHER PUBLICATIONS

Huh et al., Comparison of SpineJet XL and Conventional Instrumentation for Disk Space Preparation in Unilateral Transforaminal Lumbar Interbody Fusion. J Korean Neurosurg Soc. May 2010;47(5):370-6.

Non-Final Office Action for U.S. Appl. No. 15/631,722, dated Feb. 21, 2019, 14 pages.

* cited by examiner

COLLAGENASE I-INJECTED TENDON SAMPLES

VOLUME FRACTION (%)

| POWER SETTING | PRE-DEBRIDEMENT | | POST-DEBRIDEMENT | |
|---|---|---|---|---|
| | AVG. | ST. DEV. | AVG. | ST. DEV. |
| 5 | 5.45 | 6.06 | 0.62 | 0.86 |
| 6 | 10.54 | 2.81 | 0.91 | 0.80 |
| 7 | 4.07 | 3.45 | 1.24 | 0.99 |
| 8 | 6.77 | 3.87 | 0.94 | 1.11 |
| 9 | 14.96 | 9.00 | 0.91 | 1.32 |
| 10 | 10.38 | 0.63 | 0.24 | 0.12 |
| AVG. | 8.70 | 4.30 | 0.81 | 0.87 |

*FIG. 12*

CONTROL, PBS-INJECTED TENDON SAMPLES

VOLUME FRACTION (%)

| POWER SETTING | PRE-DEBRIDEMENT | | POST-DEBRIDEMENT | |
| --- | --- | --- | --- | --- |
| | AVG. | ST. DEV. | AVG. | ST. DEV. |
| 5 | 0.03 | 0.04 | 0.39 | 0.40 |
| 6 | 0.00 | 0.00 | 0.15 | 0.00 |
| 7 | 0.00 | 0.00 | 0.09 | 0.15 |
| 8 | 0.00 | 0.00 | 0.12 | 0.09 |
| 9 | 0.31 | 0.54 | 0.46 | 0.07 |
| 10 | 0.00 | 0.00 | 0.57 | 0.71 |
| AVG. | 0.06 | 0.10 | 0.30 | 0.24 |

*FIG. 13*

SELECTIVE TISSUE REMOVAL TREATMENT DEVICE

This application is a continuation-in-part of U.S. patent application Ser. No. 15/631,722, filed Jun. 23, 2017, which claims priority under 35 USC § 119 to U.S. Provisional Application No. 62/354,515, filed Jun. 24, 2016, the disclosures of which are herein incorporated by reference in their entirety.

BACKGROUND

The present disclosure relates to a surgical device for soft tissue treatment, including devices and methods for selectively cutting and removing tissues.

Tendon injuries are commonly caused by repeated tendon strain and can range from simple micro tears with inflammation to complete tears and ruptures. Healthy tendons include mature, highly-organized, type I collagen fibers, which are capable of withstanding relatively large tensile loads. A typical tendon injury, or tendinopathy, may be marked by an increased presence of immature, type III collagen, characterized by a loose fibril organization. Increased type III collagen disrupts type I collagen alignment, potentially leading to a loss in strength and increased water retention of the tendon, which in turn, contributes to the cycle of injury and may lead to painful nerve impingement.

In order to treat tendon or other connective tissue injuries or diseases, minimally invasive devices and techniques for selectively removing soft tissues or portions of soft tissue, like type III collagen, while leaving healthy tissue undisturbed, are desired. Conventional minimally invasive techniques may be performed using multiple instruments and entry points into the body. Such techniques may also require various compounds or equipment to enable visualization of a surgical site. A device that may reduce the number of entry points or instruments used, safely dislodge and remove pathologic tissue while leaving healthy, native tissues undisturbed, would provide significant advantages to surgeons and patients The present disclosure provides surgical devices and methods for selectively treating soft tissue.

BRIEF SUMMARY

In one embodiment, a surgical instrument for selectively removing a first tissue type includes a handle located at a proximal end of the surgical instrument adapted to be gripped by a user. The surgical instrument also includes a first lumen extending along a longitudinal axis of the surgical instrument from the proximal end to a distal end of the surgical instrument. An inner bore of the first lumen extends from an open proximal terminal end of the first lumen to a closed distal terminal end of the first lumen. The first lumen also includes a nozzle formed in a side wall proximate to the closed distal terminal end that is configured to enable a jet of fluid to exit therefrom. The nozzle has a width of approximately 0.003 to 0.015 inches.

The surgical instrument additionally includes a second lumen extending adjacent and parallel to the first lumen with an inner bore of the second lumen extending from an open proximal terminal end of the second lumen to a closed distal terminal end of the second lumen. The second lumen has an inner width greater than an inner width of the first lumen. The second lumen also includes an aperture approximately 0.055 to 0.011 inches in length and 0.040 to 0.055 inches in depth disposed adjacent to the nozzle to receive therein the jet of fluid exiting the nozzle. When the surgical instrument is in operation, the surgical instrument cuts and evacuates tissue through the aperture and inner bore of the second lumen to selectively remove a first tissue type from different tissue types located in a surgical site.

In another embodiment, a method of selectively removing a first tissue type is provided comprising selecting a power level of a surgical instrument of such that a pressure of a jet of fluid exiting a nozzle of a first lumen is approximately 2,000 to 14,000 psi. The method further comprises inserting the surgical instrument into a surgical site and operating the surgical instrument at the selected power level to create a jet of fluid, cutting and suction forces at the aperture of the second lumen. The suction is generated from pressurized fluid in the inner bore of the first lumen exiting the nozzle and entering the aperture of the second lumen. The method comprises selectively cutting and evacuating a first tissue type from two or more tissue types within the surgical site.

The surgical instrument of the method of selectively removing a first tissue type further comprises a nozzle of the first lumen approximately 0.003 to 0.015 inches in width, an aperture of the second lumen approximately 0.055 to 0.011 inches in length, and approximately 0.040 to 0.055 inches in depth. The method further comprises selectively cutting a first tissue type from two or more tissue types within the surgical site and evacuating the cut first tissue type from the surgical site through the inner bore of the second lumen of the surgical instrument.

In another embodiment, a method of treating a tendon is provided comprising selecting a tendon and imaging said tendon to identify a region of said tendon that contains tendinopathic tissue. The method further comprises selecting a surgical device having a proximal end, distal end, first lumen, and second lumen. The first lumen includes a nozzle formed in a side wall proximate the distal end of the surgical device and configured to enable a jet of pressurized fluid to exit the nozzle. The second lumen includes an aperture formed in a side wall proximate the distal end of the surgical device, disposed adjacent to the nozzle of the first lumen, configured to receive the jet of pressurized fluid exiting the nozzle.

The method of treating a tendon further comprises inserting the distal end of the surgical device proximate or within the tendinopathic tissue, powering the surgical device to create a jet of fluid and suction force at the distal end of the surgical device, and cutting and suctioning said tendinopathic tissue from adjacent, healthy tendon tissue. Finally, the method of treating a tendon comprises evacuating said tendinopathic tissue through the inner bore of the second lumen of the surgical device.

BRIEF DESCRIPTION OF THE DRAWINGS

The accompanying figures illustrate one or more embodiments of the invention. The drawings are not necessarily to scale. The present invention is illustrated by way of example, and not limitation, in the accompanying figures wherein:

FIG. 12 is a table containing average volume fractions of tendinopathic tissue before and after removal using the disclosed device, according to an example of the present disclosure.

FIG. 13 is a table containing average volume fractions of control tissue before and after removal using the disclosed device, according to an example of the present disclosure.

DETAILED DESCRIPTION

Reference will now be made in detail to various embodiments of the disclosed devices and methods, examples of which are illustrated in the accompanying drawings. Wherever possible, the same reference numbers will be used throughout the drawings to refer to the same or like parts.

In this application, the use of the singular includes the plural unless specifically stated otherwise. In this application, the use of "or" means "and/or" unless stated otherwise. Furthermore, the use of the term "including", as well as other forms, such as "includes" and "included", is not limiting. Any range described herein will be understood to include the endpoints and all values between the endpoints. Multiple will be understood to refer to two or more.

The section headings used herein are for organizational purposes only and are not to be construed as limiting the subject matter described. All documents, or portions of documents, cited in this application, including but not limited to patents, patent applications, articles, books, and treatises, are hereby expressly incorporated by reference in their entirety for any purpose.

Current minimally invasive surgical techniques may cause damage to tissues that are not targeted during a surgical procedure. The introduction of multiple entry points and introducing foreign visualization compounds to the body may create trauma that may prolong patient recovery times and increase the overall cost associated with non-invasive procedures. Current minimally invasive surgical techniques could be improved by enabling the selective removal of tissues from a surgical site. Therefore, there is a need for a method to effectively and safely remove pathologic tissues while minimizing trauma at a surgical site by using a single device, and/or to selectively remove certain types of tissue.

Embodiments of the present surgical instruments and methods allow for selective removal of tissue from a surgical site that limits the number of entry points and/or amount of foreign compound introduced into the body. In one embodiment, the surgical instrument is configured to create a cutting and suction force at the distal end of the surgical instrument. The cutting and suction force is generated from the movement of a jet of pressurized fluid from the nozzle of a first lumen to the aperture of a second lumen. The cutting and suction force selectively removes a specified tissue type from the surgical site, and the level of force may be adjusted to target a certain soft tissue by adjusting the fluid pressure travelling through a first lumen. The removed tissue is evacuated with a moving fluid through the second lumen. As such the water jet results in a cutting and suction force, thereby allowing cutting and removal of tissue with one device.

Figure 1:
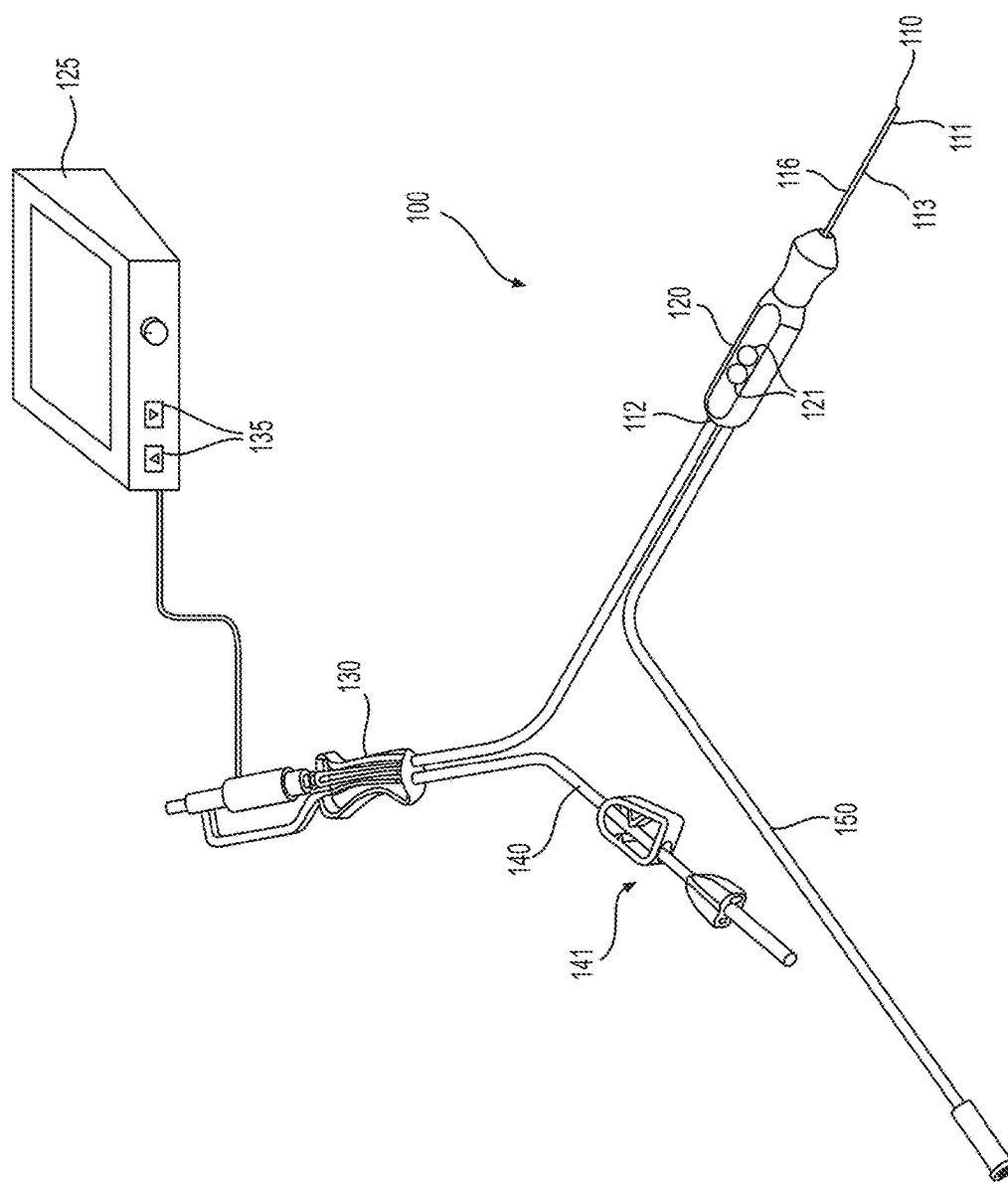
FIG. 1 illustrates a perspective view of a surgical instrument according to various embodiments of the present disclosure.

FIG. 1 is a perspective view of a surgical instrument 100 according to an exemplary embodiment. The surgical instrument 100 includes an insertion end 110 attached to a handle 120. The insertion end 110 includes a first lumen 113 and a second lumen 116 extending through or otherwise attached to the handle 120. The first lumen 113 and the second lumen 116 are depicted and described further in accord with FIGS. 2 and 3, respectively. The handle 120 and/or lumens are connected to a pump assembly 130. The pump assembly 130 provides a jet of fluid travelling through the first lumen 113 toward the insertion end 110 of the surgical instrument 100. When the jet of fluid travels from the first lumen 113 to the second lumen 116 at the distal end 111 of the surgical instrument 100, a cutting and suction force is generated, which can selectively remove tissue from a surgical site. The distal end 111 is depicted and described further in accordance with FIG. 5.

The term "lumen" as used herein will be understood to refer to a structure that includes a wall with an open passageway therethrough. Although lumen may otherwise refer to an opening or passage within a tube, it will be understood in the present disclosure to refer to the physical tube or structure itself, and the "first lumen" and "second lumen" will be understood to also include an "inner bore" as discussed below. It will also be understood that either "lumen" can be provided in a variety of configurations including cylindrical, rectangular, polygonal prismatic, or others, having uniform or irregular cross-sections along their lengths.

Further, although the first lumen 113 and second lumen 116 are illustrated as straight tubes or rod-like structures, other shapes may be used. For example, the lumens may be curved or angled to allow access to specific anatomic locations. As such, although being illustrated as straight structures, other configurations may be included.

A user may adjust the pressure of the jet of fluid with an adjustor 135. The jet of fluid is provided through a supply line 140. The jet of fluid is used to cut or resect tissue in a surgical site. Further, the pressure of the jet of fluid, controlled by the adjustor 135, can be selected to accommodate the type of tissue cut and removed from the surgical site. The cutting and removal of tissue is discussed in more detail below. Cut tissue is evacuated through evacuation lumen 150 by the movement of pressurized fluid and by vacuum forces generated by the movement of pressurized fluid from the first lumen 113 to the second lumen 116 at the distal end 111 of the surgical instrument 100.

The pump assembly 130 may be any power source connectable to the open proximal terminal end of the first lumen 113 that is suitable to create the suction force at an aperture or opening 118 of the second lumen 116. The aperture or opening 118 is depicted and described further in accord with FIG. 3. The pump assembly 130 may be a pump cartridge, peristaltic pump, a configuration with a piston for pumping the jet of fluid through the surgical instrument 100, or any other pump suitable for generation of the jet. The piston may be powered by a transmission or any other suitable powering means. In one embodiment, the pump assembly 130 delivers a pressurized jet of fluid. In one embodiment, the jet of fluid is water. In another embodiment, the jet of pressurized fluid is saline. As an example, the pump assembly 130 may pump a fluid into the first lumen 113 to form the jet of fluid exiting a nozzle or opening 115. The nozzle or opening 115 is depicted and described further in accord with FIG. 2.

The supply line 140 may include an inlet line adapted to connect with a fluid source. In one embodiment, the supply line includes a spike or other connector (e.g., Luer, threaded, or other connector) to attach to a fluid source. In one embodiment, the fluid source is an IV bag of fluid. The supply line 140 may further include a line clamp 141 configured to stop flow of the fluid from the fluid source. The supply line 140 may be composed of high pressure tubing.

In some embodiments, the magnitude of the cutting and suction force generated in the surgical instrument 100 may be controllable by a user of the surgical instrument. In one embodiment, the magnitude of the cutting and suction force produced in the surgical instrument 100 may be controlled by the user of the surgical instrument through a console 125. The console 125 may be a computing device or a mechanical device. For example, a console 125 may include an adjustor 135 operable to control the pressure of the fluid provided to the first lumen 113. The pressure of fluid travelling through the first lumen 113 can affect or determine the amount of force generated at the distal end 111 of the surgical instrument 100. between the first lumen 113 and second lumen 116.

In one embodiment, the adjustor 125 may be a keypad in digital or mechanical communication with the pump assembly 130 and able to send commands to the pump assembly 130. In another embodiment, the console 125 may be a user interface provided by a tablet or other computing device, and the adjustor 135 may be a user interface element displayed thereon that is operable to accept commands for controlling the pump assembly 130. It will be appreciated that in other embodiments, the adjustor 135 may be a mechanical device such as a clamp or similar device operable on the fluid line being provided to the surgical instrument 100 without the use of a console 125. The adjustor 135 is discussed further below.

Alternatively, in another embodiment, the surgical instrument 100 may be configured to operate at a pre-determined magnitude of fluid pressure and suction force in such a case may not be adjustable by a user of the surgical instrument. In addition, in other embodiments, a controller is placed elsewhere to enable more convenient access to a user. For example, in one embodiment, the handle 120 is equipped with controllers 121, which allow manual adjustment directly by a user (e.g., by controlling a valve or other mechanism within the device). Alternatively, or additionally, the instrument 100 can include other control mechanisms, e.g., foot pedals, to allow control without interruption of a procedure by the user holding the instrument 100.

Figure 2:
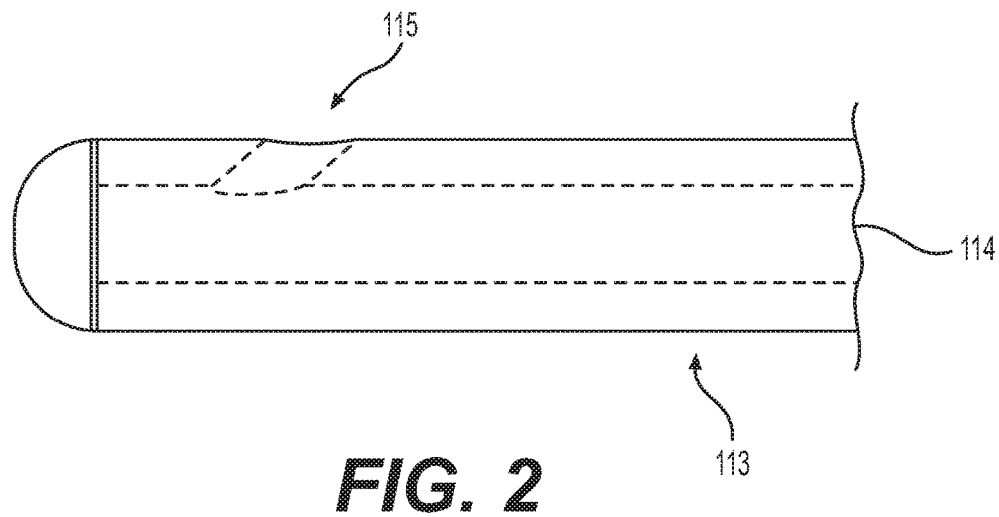
FIG. 2 illustrates a side view with hidden lines visible of a first lumen of the surgical instrument according to various embodiments of the present disclosure.

FIG. 2 is a side view with hidden lines visible of a first lumen 113 of the surgical instrument 100 according to an exemplary embodiment. The first lumen 113 extends along a longitudinal axis of the surgical instrument 100 from a proximal end 112 of the handle 120 to a distal end 111 of the surgical instrument 100. Inner bore 114 of the first lumen 113 extends from an open proximal terminal end of the first lumen 113 to a closed distal terminal end of the first lumen 113. The first lumen 113 guides fluid from the pump assembly 130 to the nozzle or opening 115. The nozzle or opening 115 is formed in a side wall proximate to the closed distal terminal end of the first lumen 113.

In some embodiments, the inner width of the first lumen 113 is about between 0.005 and 0.050 inches. In certain embodiments, the inner width of the first lumen 113 is 0.013 inches. A variety of inner width lengths are suitable for first lumen 113, and can be configured to optimize efficacy and performance of the disclosed tissue removal device.

In some embodiments, the width of nozzle or opening 115 is configured to provide adequate removal of pathologic tissue from a tendon exhibiting symptoms of tendinopathy. The width of nozzle or opening 115 can be about, more than, or less than 0.0001, 0.0005, 0.001, 0.002, 0.003, 0.004, 0.005, 0.006, 0.007, 0.008, 0.009, 0.010, 0.011, 0.012, 0.013, 0.014, 0.015, 0.016, 0.017, 0.018, 0.019, 0.020, 0.025, 0.030, 0.035, 0.040, 0.045, 0.050, or 0.010 inches. These values can be used to define discrete lengths, such as 0.005 or 0.008 inches. These values can also be used to define a range of nozzle or opening 115 widths, such as from about 0.003 to about 0.013 inches, or from about 0.007 to 0.010 inches.

According to various embodiments, the nozzle or opening 115 can be provided in a variety of shapes. For example, the nozzle or opening 115 may be provided as a void within the wall of first lumen 113, in a cylindrical, cubic, prismatic, or pyramidal shape. In some embodiments, the nozzle or opening 115 comprises a prismatic shape consisting of a triangular, rectangular, pentagonal, or higher order polygonal prism. In embodiments where the nozzle or opening 115 is provided in cylindrical form, the width of the nozzle of opening 115 comprises a diameter. The nozzle or opening 115 can assume various shapes, provided that the jet of pressurized fluid exiting the nozzle or opening 115 enters aperture 118 of second lumen 116.

In certain embodiments, the distal end of the nozzle or opening 115 is disposed at a suitable distance from the distal end of the first lumen 113. The distance between the distal end of the nozzle or opening 115 from the distal end of first lumen 113 can be about, more than, or less than 0.005, 0.010, 0.015, 0.020, 0.025, 0.030, 0.035, 0.040, 0.045, 0.05, 0.06, 0.07, 0.08, 0.09, 0.10 inches. These values can be used to define discrete distances or distances ranges. For example, in some embodiments, the distance between the distal end of the nozzle or opening 115 from the distal end of first lumen 113 is 0.015 inches, but variations may occur depending on the dimensions of surgical instrument 100.

The open, proximal terminal end of the first lumen 113 may be connectable to an energy source console. The energy source console is configurable to drive the surgical instrument 100 with an adjustable power level to adjust the cutting and suction force at the distal end 111 of the surgical instrument 100. In some embodiments, the energy source console includes the pump assembly 130, supply line 140, and the adjustor 135.

Figure 3:
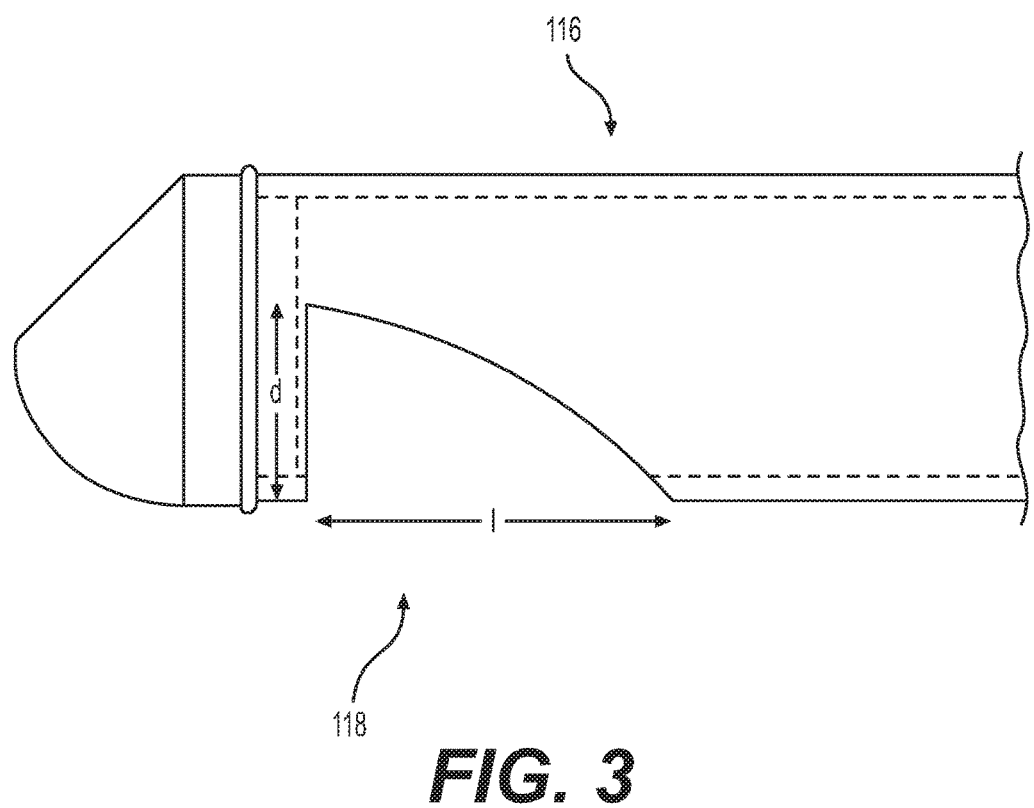
FIG. 3 illustrates a side view with hidden lines visible of a second lumen of the surgical instrument according to various embodiments of the present disclosure.

FIG. 3 is a side view with hidden lines visible of a second lumen 116 of the surgical instrument 100 according to an exemplary embodiment. The second lumen 116 includes an aperture or opening 118 configured to receive the jet of fluid travelling through nozzle or opening 115 of the first lumen 113.

In one embodiment, the inner width of the second lumen 116 is configured to accommodate aperture or opening 118 to cooperatively operate with nozzle or opening 115 of first lumen 113. The second lumen 116 can an inner width of about, more than, or less than 0.005, 0.01, 0.02, 0.03, 0.04, 0.05, 0.06, 0.07, 0.08, 0.09, 0.10, 0.15, 0.20, 0.25 or 0.50 inches. These values can be used to define a discreet inner width, such as 0.05 inches. Additionally, these values can be used to define a range of inner widths, such as 0.04 to 0.06 inches.

In some embodiments, aperture or opening 118 has a length configured to adequately receive the jet of fluid traveling through nozzle or opening 115 of the first lumen 113. FIG. 3 includes length "l" that identifies the length of aperture 118. The lengths of aperture or opening 118 be about, more than, or less than 0.020, 0.025, 0.030, 0.035, 0.040, 0.045, 0.050, 0.055, 0.060, 0.065, 0.070, 0.075, 0.080, 0.085, 0.090, 0.095, 0.10, 0.11, 0.12, 0.13, 0.14, 0.15, 0.20, 0.25, 0.30, 0.35, 0.40, 0.45, or 0.50 inches. These values can define a discrete length, such as 0.065 or 0.045 inches. Additionally, these values can be used to define a range of lengths, such as 0.055 to 0.11 inches, or 0.080 to 0.095 inches.

In some embodiments, aperture or opening 118 has a depth configured to adequately receive the jet of fluid traveling through nozzle or opening 115 of the first lumen 113. FIG. 3 includes depth "d" that identifies the depth of aperture 118. The depth of aperture or opening 118 can be about, more than, or less than 0.005, 0.01, 0.02, 0.03, 0.04, 0.045, 0.05, 0.055, 0.06, 0.065, 0.07, 0.075, 0.08, 0.09, 0.10, 0.105, 0.11, 0.115, 0.12, 0.13, 0.14, or 0.15 inches. These values can define a discrete depth, such as 0.045 inches. Additionally, these values can be used to define a range of depths, such as 0.040 to 0.055 inches. The depth of aperture or opening 118 will be less than the outer width of second lumen 116.

In some embodiments, the distal end of the aperture or opening 118 is disposed about, more than, or less than 0.02, 0.03, 0.04, 0.05, 0.06, 0.07, 0.08, 0.09, 0.10, 0.20, 0.30 inches from the distal end of the second lumen 116. These values can be used to define discrete distances or range of distances. For example, in certain embodiments, the distal end of the aperture or opening 118 is disposed 0.081 or 0.065 inches from the distal end of the second lumen 116.

In one embodiment, the open proximal terminal end of the second lumen 116 is connectable to the evacuation lumen 150. In one embodiment, the second lumen 116 is connected to the evacuation lumen 150 through the handle 120, as depicted in FIG. 1. Tissue and fluid received by the second lumen 116 is transported through inner bore 117 of second lumen 116 to the evacuation lumen 150. In some embodiments, the evacuation lumen 150 is in communication with a receptacle for storing biological materials, such as tissue and fluid.

Figure 4A:
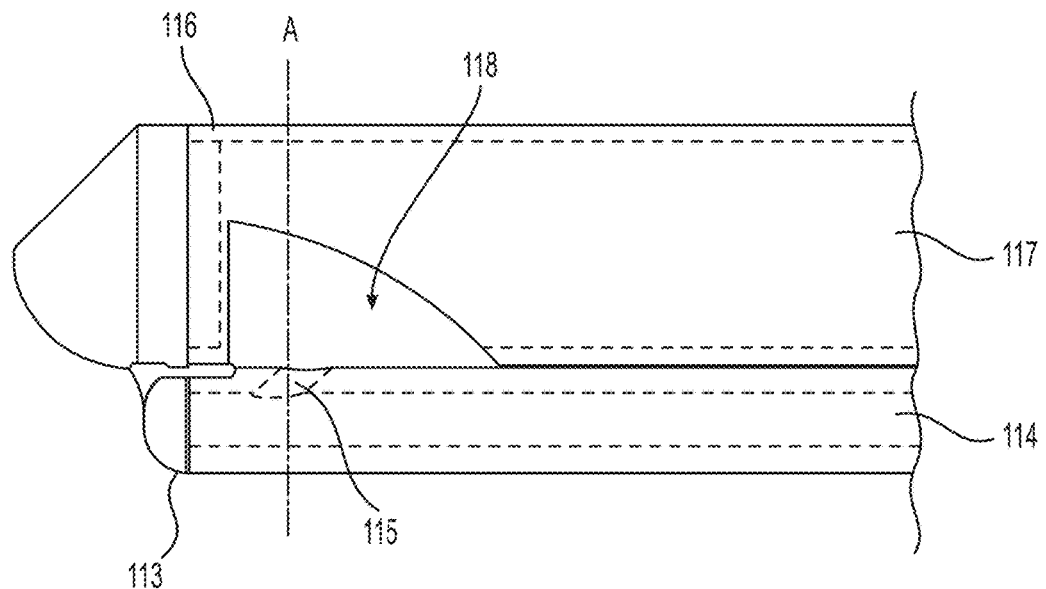
FIG. 4A illustrates a side view with hidden lines visible of an assembled first lumen and second lumen of the surgical instrument according to various embodiments of the present disclosure.

FIG. 4A is a side view with hidden lines visible of an assembled first lumen 113 and second lumen 116 of the surgical instrument 100 according to an exemplary embodiment. The second lumen 116 is disposed parallel to the first lumen 113 such that the aperture or opening 118 is disposed across from or otherwise aligned with the nozzle or opening 115 and configured to receive the jet of fluid. The second lumen 116 extends parallel to the first lumen 113 along the longitudinal axis of the surgical instrument 100, an inner bore 117 of the second lumen 116 extending from an open proximal terminal end of the second lumen 116 to a closed distal terminal end of the second lumen 116. The jet of fluid passing through nozzle 115 to aperture 118 generates a cutting and suction force at the distal end 111 or surgical instrument 100. Creation of the cutting and suction force is described in more detail below.

Figure 4B:
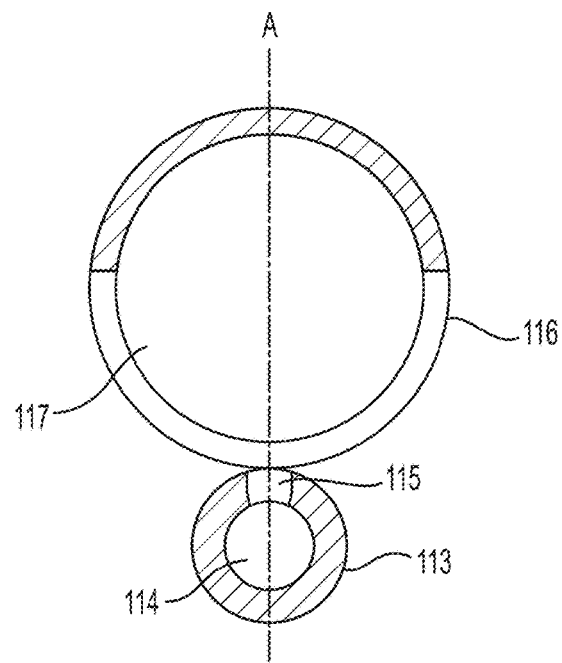
FIG. 4B illustrates a cross-sectional view of an assembled first lumen and second lumen of the surgical instrument according to various embodiments of the present disclosure.

FIG. 4B is a cross-section view of an assembled first lumen 113 and second lumen 116 of the surgical instrument 100 according to an exemplary embodiment. In some embodiments, the second lumen 116 has an inner width greater than an inner width of the first lumen 113. In various embodiments, the width of nozzle or opening 115 is smaller than the width of the aperture or opening 118. In certain embodiments, the first lumen 113 is connected to the second lumen 116 by mechanical fixation, e.g., by welding, clamping, or forming as a unitary structure.

Figure 5:
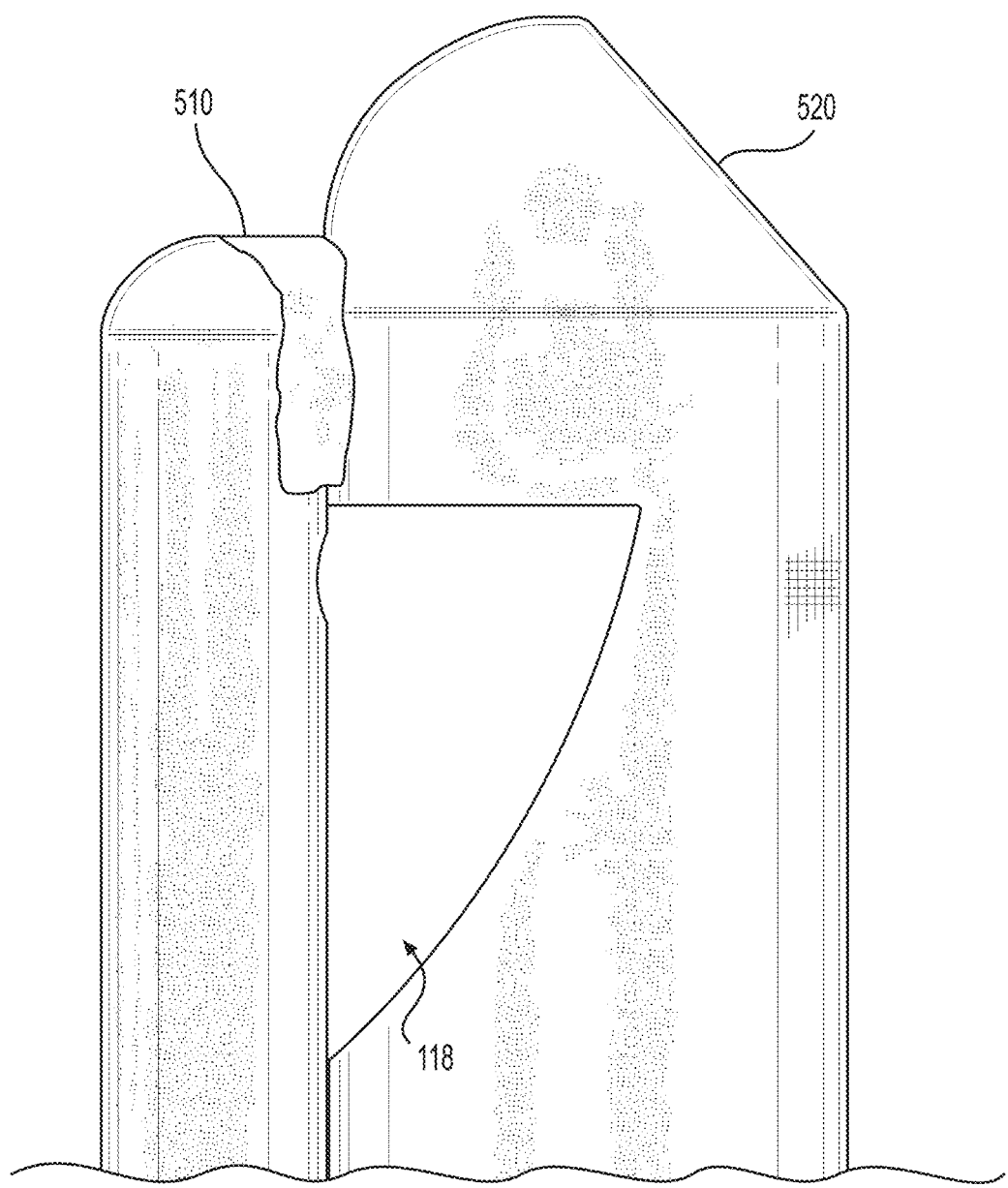
FIG. 5 illustrates a side view of the distal end of the surgical instrument according to various embodiments of the present disclosure.

FIG. 5 is a side view of the distal terminal end 111 of the surgical instrument 100, according to an exemplary embodiment. In one embodiment, distal terminal ends 510 and 520 of the first lumen 113 and the second lumen 116, respectively, are closed. In certain embodiments, the closed distal terminal end 510 of the first lumen 113 is shaped to assist moving the insertion end 110 through tissue of a patient. For example, the insertion end 110 may be inserted through dermal, fascial, muscular, adipose, or connective tissue (or other tissue) to reach a surgical site. In one embodiment, the closed distal terminal end 520 of the second lumen 116 extends further than the closed distal terminal end of the first lumen 113. In an embodiment, the closed distal terminal end 520 of the second lumen 116 is pointed or beveled.

In one embodiment the insertion end 110 may be guided with the aid of ultrasound or other suitable imaging techniques. In an embodiment, ultrasound may be used to identify pathologic tissue in a joint or other structure without the aid of fluids. Pathologic tissue may be scar tissue, diseased tissue, dead tissue, inflamed tissue, or otherwise undesirable tissue. Pathologic tissue may also include ligaments, hematomas, debrided cartilage, and loose tissue in and around the joint. The insertion end 110 may be guided to the pathologic tissue to remove the identified tissue with a cutting and suction force. In another embodiment, the pathologic tissue is type III collagen.

In certain embodiments, diseased tissue or tissue otherwise desirable to remove is identified in an elbow joint or other musculo-skeletal structure. In some embodiments, the angle of the nozzle or opening 115, alignment of insertion end 110 and aperture or opening 118, with relation to second lumen 116 and the surgical site prevents dense tissue from being cut and removed by surgical instrument 100 because, in certain cases, it is too fibrous or is otherwise not as easily cut or removed as other tissue. For example, type I collagen has a highly aligned and densely packed structure, capable of withstanding high tensile and shear forces. In contrast, pathologic tissue, such as type III collagen, is less uniformly aligned and is not capable of withstanding large mechanical forces. As such, type III collagen may be removed at suction levels that may leave nearby type I collagen undisturbed.

In an embodiment, the surgical instrument 100 is suitable for use in different types of living tissue. In certain embodiments, the surgical instrument 100 is suitable for use in human tissue. In some embodiments, the surgical instrument 100 is suitable for use in joints or other musculo-skeletal structures.

In one embodiment, the surgical instrument 100 may be used to remove pathologic tissue from joints. In one example, the surgical instrument 100 may be used to remove pathologic tissue from tendons in elbow joints. The suction force can be adjusted to draw in or remove only selected tissue types, such as type III collagen or other tissue that is potentially pathologic, without disturbing other tissue types in the surgical site, such as type I collagen of healthy tendons. Specifically, different types of tissue withstand different thresholds of cutting and/or suction forces, so by controlling the fluid jet pressure and the resultant cutting and suction forces, the types of tissue being removed from the surgical site can be controlled.

In some embodiments, the surgical instrument 100 may be utilized to remove pathologic tissue from different areas of the body, including without limitation, elbow, shoulder, knee, hip, ankle, or wrist joints. In one embodiment, the surgical instrument 100 may be utilized for removal of soft tissue in orthopedic procedures.

Figure 6:
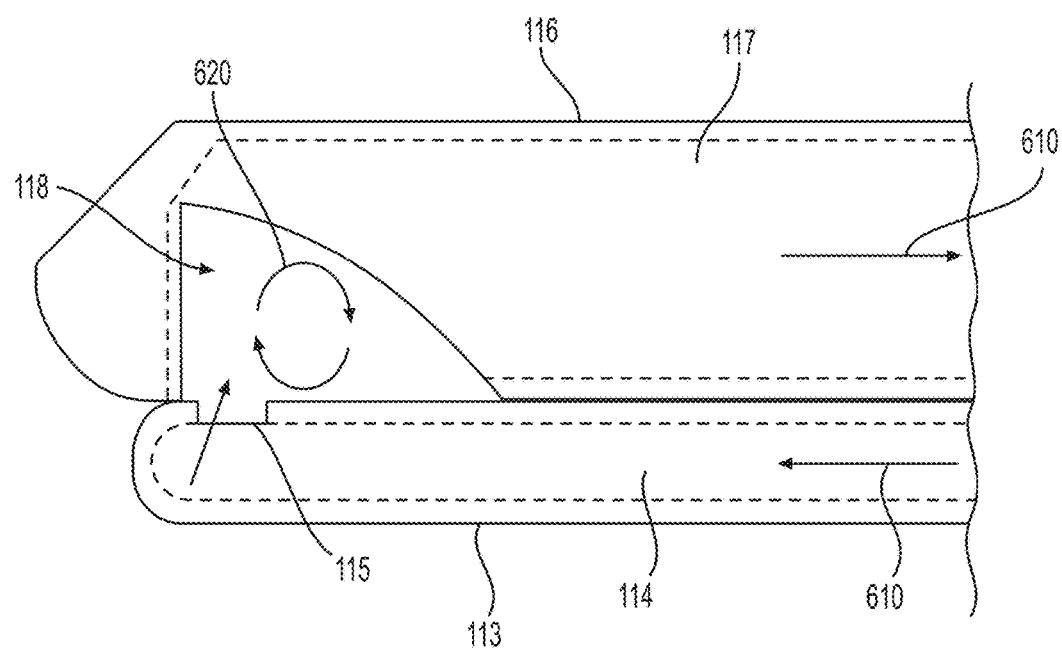
FIG. 6 illustrates a side view with hidden lines visible of a jet of fluid traveling through the surgical instrument according to various embodiments of the present disclosure.

FIG. 6 is a side view with hidden lines visible of a jet of fluid 610 traveling through the surgical instrument 100 according to an exemplary embodiment. The fluid jet force 620 is created when the jet of fluid 610 enters the aperture or opening 118 from the nozzle or opening 115. The jet of fluid 610 is a type of fluid capable of being pressurized and dispersed through the nozzle 115. In some embodiments, the fluid is water or saline. In an embodiment, the jet of fluid 610 may leave the nozzle or opening 115 at a 55° angle relative to the opposing aperture or opening 118 of the second lumen 116 of the surgical instrument 100. However, additional angles may be suitable for the surgical instrument 100 of the present disclosure, including approximately 20°, 25°, 30°, 35°, 40°, 45°, 50°, 55°, 60°, 65°, or 70°. These values can be used to define discreet angles, such as 50°, or ranges of angles, such as 45° to 55°.

The jet of fluid 610 provided through supply line 140 may have a pressure set using the adjustor 135 and console 125 (or other control means) to produce adequate cutting and/or suction at the distal end 111 to safely cut or resect pathologic tissue. The pressure of the jet of fluid 610 can be about, more than, or less than 100, 200, 400, 600, 800, 1,000, 2,000, 2,500, 3,000, 3,500, 4,000, 4,500, 5,000, 5,500, 6,000, 6,500, 7,000, 7,500, 8,000, 8,500, 9,000, 9,500, 10,000, 12,000, 14,000, 16,000, 18,000, or 20,000 psi. These values can be used to define a range, such as that from about 2,000 to about 14,000 psi, or from about 6,000 to 18,000 psi.

The cutting and/or suction force may be increased by increasing the pressure of the jet of fluid 610. As noted above, the pressure of the jet of fluid 610 may be increased or decreased by a user of the surgical instrument 100 via an adjustor 135. In one embodiment, the adjustor may be a manual tab for adjusting a power level of the surgical instrument 100, such as a wheel, knob, or lever. In some embodiments, the adjustor 135 has a fixed number of settings designating predetermined pressures for the jet of fluid 610. Table 1 illustrates exemplary pressure levels for fluid within the jet.

TABLE 1

Exemplary power levels and corresponding average pressures

| Power Level | Average Pressure (psi) |
|---|---|
| 1 | 2395 |
| 2 | 3574 |
| 3 | 4880 |
| 4 | 6244 |
| 5 | 7662 |
| 6 | 9078 |
| 7 | 10498 |
| 8 | 12020 |
| 9 | 13082 |
| 10 | 14065 |

In one embodiment, the pressure of the jet of fluid 610 pumped through the surgical instrument 100 ranges from 2,395 psi to 14,065 psi. In another embodiment, the pressure of the jet of fluid 610 ranges from 2,395 psi to 12,020 psi, or from 2,000 to 12,000 psi. It will be appreciated that other pressure ranges of greater and lesser values are also within the scope of the present disclosure.

The adjustor 135 (or other component) may include an adjustment means for adjusting the pressure of the jet of fluid 610 through the pump assembly 130. The adjustment means may be at least one knob, button, lever, keypad, or any other suitable means for adjusting the pressure of the jet of fluid 610. In some embodiments, the adjustment means enables a user of the surgical instrument 100 to select a predetermined power level, corresponding to a fluid pressure. In certain embodiments, the user can select one of ten power levels. In one embodiment, the surgical instrument 100 is configured to provide a predetermined pressure and does not include an adjustor.

Figure 7:
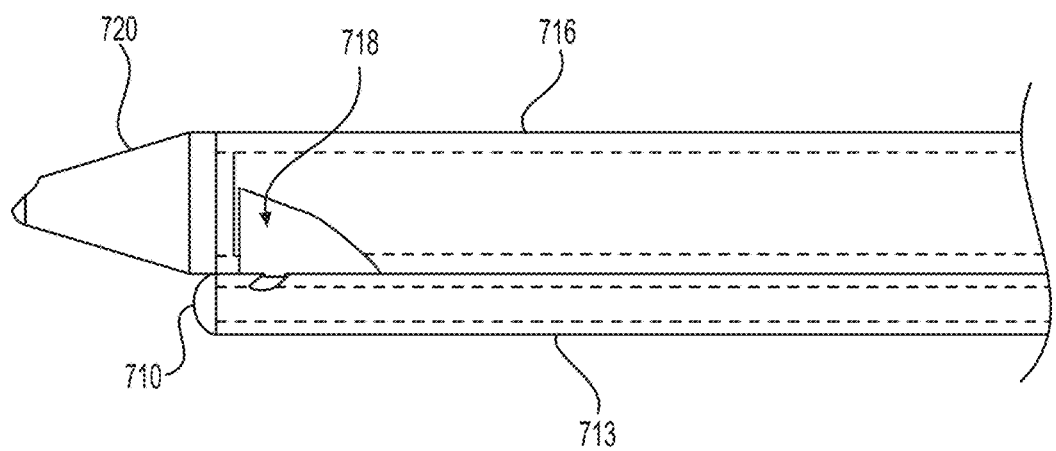
FIG. 7 illustrates a side view with hidden lines visible of an alternative configuration of the distal end of the surgical instrument according to various embodiments of the present disclosure.

FIG. 7 illustrates a side view with hidden lines visible of an alternative configuration of the distal end of the surgical instrument according to various embodiments of the present disclosure. First lumen 713 comprises distal terminal end 710 provided in a rounded configuration to enable atraumatic insertion of the instrument into and through the tissue of a patient. Second lumen 716 comprises aperture 718 configured to receive a jet of fluid from first lumen 713. Second lumen 716 also comprises distal terminal end 720, provided in a variety of configurations. In some embodiments, distal terminal end 720 is provided in needle-like or pointed configuration. Distal terminal end 720 can be formed in a variety of ways, including grinding or casting, and can be attached to the surgical instrument in a variety of ways, including via welding.

In some embodiments, the distal terminal end 720 may be inserted through a variety of tissues during use of the surgical instrument. For example, distal terminal end 720 may be configured to guide the surgical instrument through dermal, fascial, muscular, adipose, or connective tissue (or any other anatomic tissue) to reach a surgical site. The degree of sharpness of distal terminal end 720 is such that is can move easily through patient tissue.

Figure 8:
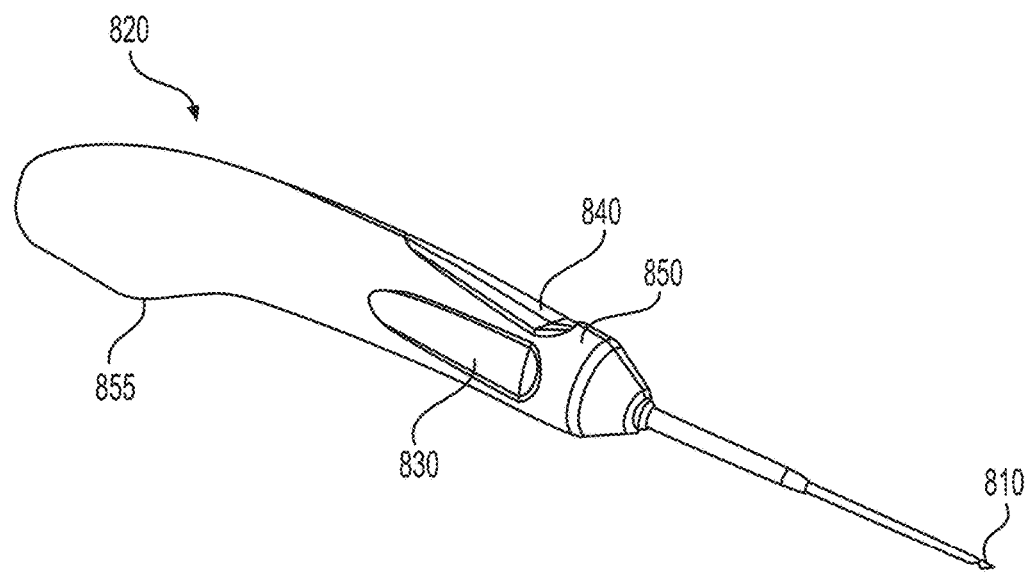
FIG. 8 illustrates a perspective view of a surgical instrument according to various embodiments of the present disclosure including a handle shaped for ergonomic use.

The shape of the handle of the disclosed device can be configured to assist users in maneuvering and guiding the surgical device of the present disclosure through patient tissue to the surgical site or to make the instrument ergonomic or comfortable to hold. For example, FIG. 8 illustrates a perspective view of a surgical instrument, according to various embodiments of the present disclosure, including a handle shaped for ergonomic use. In various embodiments, handle 820 is provided in an ergonomic configuration.

Handle 820 is configured so it is comfortable to hold and manipulate by users, such as surgeons.

In some embodiments, handle 820 comprises finger rests 830, 840, on which a user can position one or more finger fingers. In some embodiments, flange 850 acts as a stop on which users can rest the tops of their fingers for improved instrument control. Flange 850 can also prevent user fatigue by reducing bending of the finger joint. Rear jut 855 provides a rest for proximal ends of a user's hand. In some embodiments, the shape of handle 820 is such that the surface area of the handle in contact with the user's hand is controlled to reduce points of high pressure, which can also results in user fatigue. Additionally, in various embodiments, handle 820 is configured to provide users enhanced control of distal tip 810 during a procedure by increasing the contact area between a user's hand and handle 820.

Figure 9:
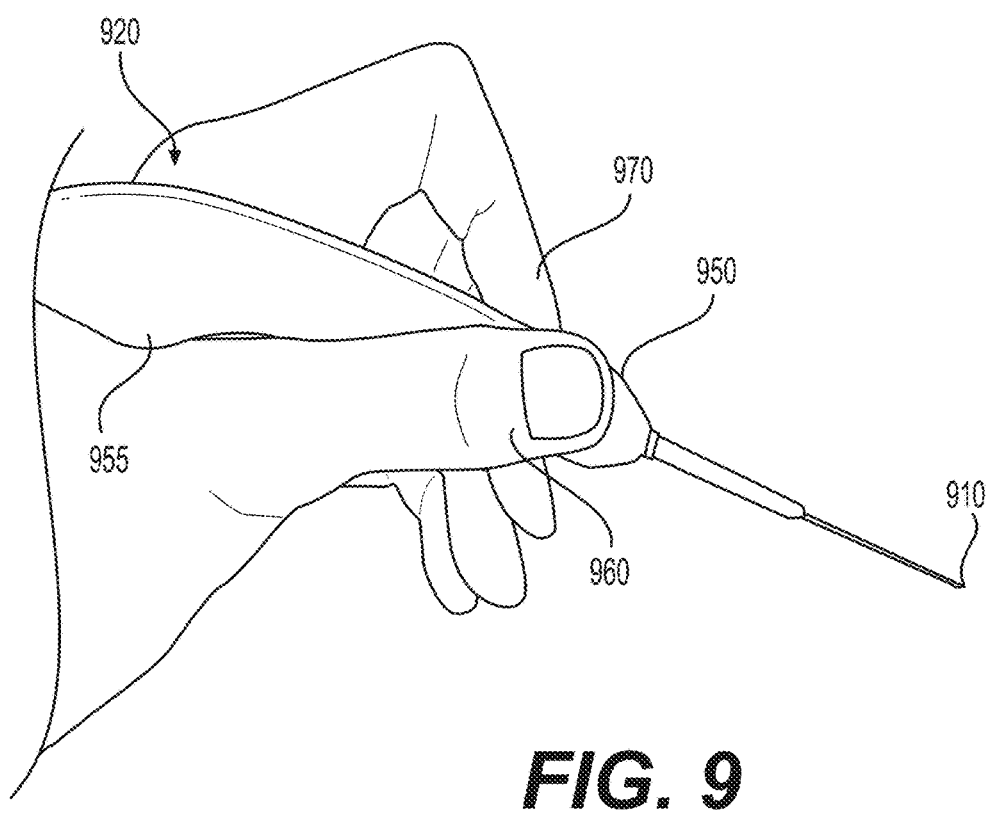
FIG. 9 illustrates a user holding a surgical instrument, according to various embodiments of the present disclosure.

FIG. 9 illustrates a user holding a surgical instrument, according to various embodiments of the present disclosure. Handle 920 is configured ergonomically to enhance user experience and improve comfort during use of the surgical device. FIG. 9 illustrates one embodiment of a pen-type grip, also referred to as a tri-pod grip, that can be used in accordance with the disclosed device. The pads of thumb 960 and index finger 970 are positioned, in part, in separate finger rests (pictured in FIG. 8). Further, the tops of thumb 960 and index finger 970 abut and rest on flange 950, and rear jut 955 rests proximate the webbing between thumb 960 and index finger 970. The increased contact area and surface features of handle 920 result in a comfortable, ergonomic gripping experience for users and enable enhanced manipulation of distal tip 910 of the surgical instrument. Additionally, other grip types may be used with the surgical instrument of the present disclosure, including, but not limited to any variation of pronated grips, which resemble the grip used to hold a screwdriver.

Figure 10:
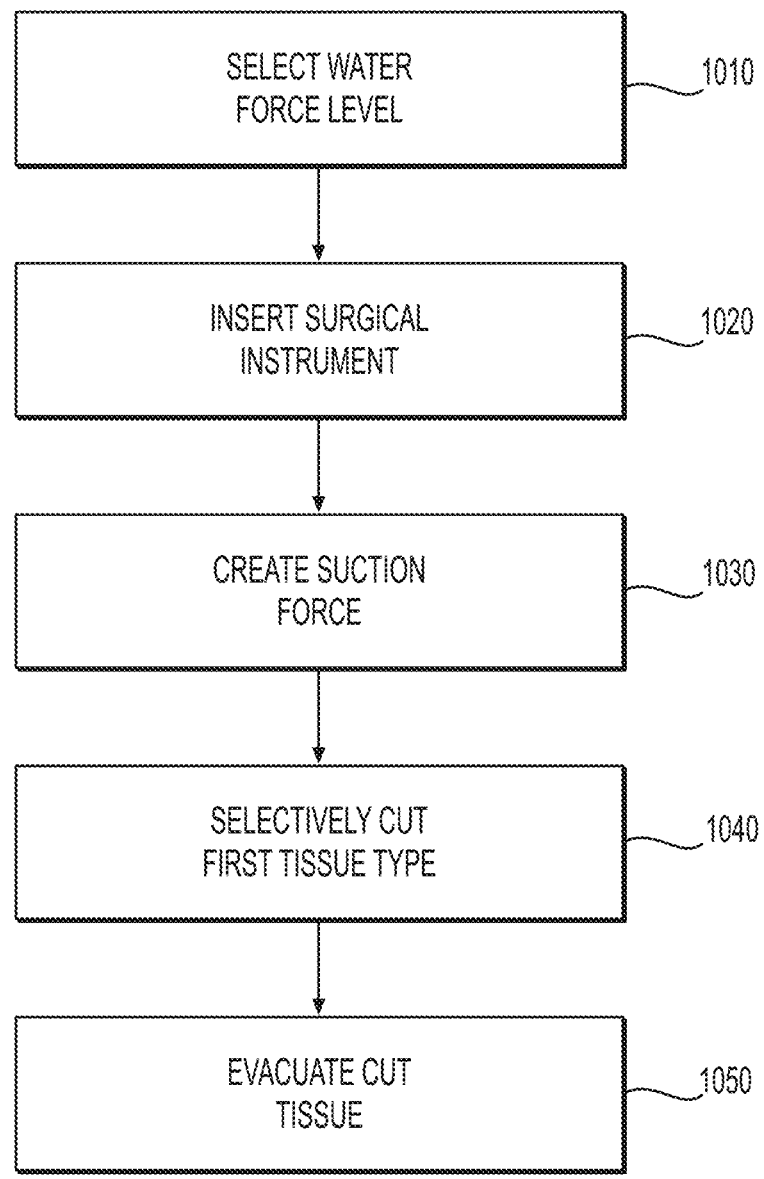
FIG. 10 illustrates an exemplary sequence in a method of removing a selected tissue from a surgical site, according to various embodiments of the present disclosure.

FIG. 10 is a flowchart depicting an exemplary sequence in a method of removing a selected tissue from a surgical site according to an exemplary embodiment. The method begins after a surgical site is selected at Step 1010 when a fluid pressure level is selected by a user of the surgical instrument. For example, the user may use an adjustor on the surgical instrument 100 to select a pre-determined power level. A suitable surgical site may be a joint in a patient. In one embodiment, the surgical site is an elbow joint. The fluid pressure level can be selected after at least a first tissue type is identified within the surgical site so that an appropriate suction force level is determined, or based on expected levels for known tissue types. The tissue type may be identified through ultrasound or other suitable imaging techniques, or by surgical experience or visual inspection. In some embodiments, multiple tissue types are identified.

At Step 1020, a surgical instrument 100 is inserted into the surgical site. In one embodiment, an incision or puncture is made in a surgical site to allow insertion of the surgical instrument. In an embodiment, the surgical instrument 100 may be shaped to move through tissue of a patient. In another embodiment, a closed distal terminal end 520 of the second lumen 116 of the surgical instrument 100 is shaped to move through tissue of a patient.

At Step 1030, a cutting and suction force is created within the surgical site using the surgical instrument 100 operating at a selected fluid pressure level. In one embodiment, the suction force is created by pumping a pressurized fluid through the inner bore 114 of the first lumen 113. In another embodiment, the suction force is created by pumping pressurized fluid through a nozzle or opening 115 of a first lumen 113 into an aperture or opening 118 of a second lumen 116 of the surgical instrument 100. In an embodiment, the fluid is a jet of fluid 610. As described herein, in one embodiment, the pressure of the jet of fluid 610 may be adjusted to control the magnitude of the cutting or suction force generated at distal end 111 of surgical instrument 100.

At Step 1040, the first tissue type is selectively cut or resected from the surgical site as a result of operation of the surgical instrument 100 at a selected power level. As an example, pathologic tissue, such as type III collagen, can be removed from an elbow joint without removing type I collagen tissue by creating a cutting and/or suction force of sufficient strength to resect type III collagen without resecting type I collagen.

At Step 1050, the cut or resected first tissue type is evacuated from the surgical site through inner bore 117 of second lumen 116. In some embodiments, the cut or resected first tissue type is evacuated from the surgical site with fluid. In some embodiments, the cut or resected first tissue type and the fluid are evacuated through the inner bore 117 of the second lumen 116 of the surgical instrument 110 to an evacuation lumen 150.

The tissue type(s) may be defined by a tissue density or other tissue property. For example, if a tendon or other tissue has been damaged or is diseased, the tendon may include more than one type of tissue, as the term "tissue type" should be presently understood. In one embodiment, the different tissue types may refer to healthy tissue and diseased tissue. In another embodiment, different tissue types may be identified by variations in tissue density (e.g., due to damage, disease, inflammation, etc). For example, a tendon may comprise different tissue types, including tendinopathic tissue or scar or damaged tissue in or around the tendon, and these tissue types may have variations in density. To accelerate healing, the tendinopathic or scar tissue may be removed from the tendon using the disclosed device.

In an additional example, healthy tendon will be understood to have a first density while diseased tissue may have a second density, and as such, different tissues can be identified within a common anatomic structure (e.g., a single tendon), or in a separate structure (e.g., a tendon and surrounding or nearby scar). In some embodiments, healthy tissues may have densities, for example, from approximately 1,900 kg/m$^3$ to 1,700 kg/m$^3$, while a second tissue type associated with the same tendon, but being damaged or diseased may have a density, for example, from approximately 1,100 kg/m$^3$ to 1,400 kg/m$^3$; approximately 1,200 kg/m$^3$ to 1,350 kg/m$^3$; or other ranges therebetween.

Certain types of tendinopathy may be treated using the disclosed devices and methods. For example, calcific tendinopathy of the shoulder, elbow, knee, hip, ankle, wrist, or other joints may be treated. Calcific tendinopathy occurs when calcium deposits accumulate in or around a tendon, for example, in the supraspinatus tendon of the shoulder. These calcium deposits result in inflammation, which can lead to substantial shoulder pain and inhibit joint function. To prevent further inflammation and pain, the disclosed device can be used to remove the calcium deposits.

Since certain changes may be made without departing from the scope of the present invention, it is intended that all matter contained in the above description or shown in the accompanying drawings be interpreted as illustrative and not in a literal sense. Practitioners of the art will realize that the sequence of steps and architectures depicted in the figures may be altered without departing from the scope of the present invention and that the illustrations contained herein are singular examples of a multitude of possible depictions of the present invention.

The foregoing description of example embodiments of the invention provides illustration and description, but is not intended to be exhaustive or to limit the invention to the precise form disclosed. Modifications and variations are possible in light of the above teachings or may be acquired from practice of the invention. For example, while a series of acts has been described, the order of the acts may be modified in other implementations consistent with the principles of the invention. Further, non-dependent acts may be performed in parallel.

It should be appreciated that the various embodiments individually described herein may be practiced in combination in certain circumstances without departing from the scope of the present invention. Other embodiments will be apparent to those skilled in the art from consideration of the specification and practice of this disclosure. It is intended that the specification and examples be considered as exemplary only, with the true scope and spirit of the disclosed devices and methods being indicated by the claims.

Example I: Tendinopathy Treatment Model

The following experiment demonstrates that the disclosed devices are capable of selectively removing collagen with different densities.

An in vitro study was performed to determine the ability of the disclosed device to remove pathologic tissue.

Initially, bovine flexor tendons from the ankle joint were harvested and characterized. Ultrasound was used to measure the density of the harvested tendon, which was measured to be approximately 1,900 kg/m$^3$. Tendons were separated into three groups, and subjected to injections of clostridial collagenase type 1 (290 units/mg, SIGMA-ALDRICH CORP.) in a dose escalation study from 1, 10, and 50 mg/ml. No collagenase was administered to a fourth, control group.

Following collagenase treatment, there was a significant decrease in tendon density in a dose-dependent manner. The tendon density of the 1 mg/ml group dropped from approximately 1,900 kg/m$^3$ to approximately 1,500 kg/m$^3$ after 24 hours. 72 hours after collagenase injection, the density further decreased to approximately 1,400 kg/m$^3$. The tendon group that was administered 50 mg/ml doses showed a similar pattern, resulting in complete degradation after 3 days.

The 1, 10, 50 mg/ml, and control groups were treated using the disclosed device and methods at various pressure settings. The untreated, control tendon group was resistant to removal of tissue up to the highest pressure setting. Additionally, neither tissue injury nor removal of any kind occurred. The 1 mg/ml group demonstrated similar results when treated with the disclosed device. Minimal tissue removal was observed, until the highest settings were tested. Removal of low density tissue was observed when the 10 and 50 mg/ml collagenase dosage tendon groups were treated with the disclosed device. Particularly, removal of tissue with densities less than around 1,200 to 1,300 kg/m$^3$ was achieved.

The foregoing experiment indicated that the disclosed device was able to selectively resect tissues. Particularly, the disclosed device exhibited the capability to safely remove lower-density soft tissue while leaving higher-density soft tissue unperturbed.

Example II: Supplementary Tendinopathy Treatment Model

The following example presents a study designed to determine the effectiveness of the disclosed device in removing pathologic tissue from healthy tendon. The disclosed device was used on tendinopathic and control tendons at various power levels. The levels of tendinopathic tissue in each sample were observed before and after treatment with the disclosed device. The results of this study are illustrated in the accompanying figures.

Differences between healthy and tendinopathic tendon tissue present in a number of ways. Generally, healthy tendon tissue is more dense, with compact tendon fibers possessing a high degree of alignment. Tendinopathic tendon tissue is generally less dense, with more loosely arranged and more poorly aligned tendon fibers. Various methods can be used to observe these differences. For example, H&E staining of cross-sectional slices of tendon can be used to observe tendon fiber density, compactness, and alignment.

Figure 11:
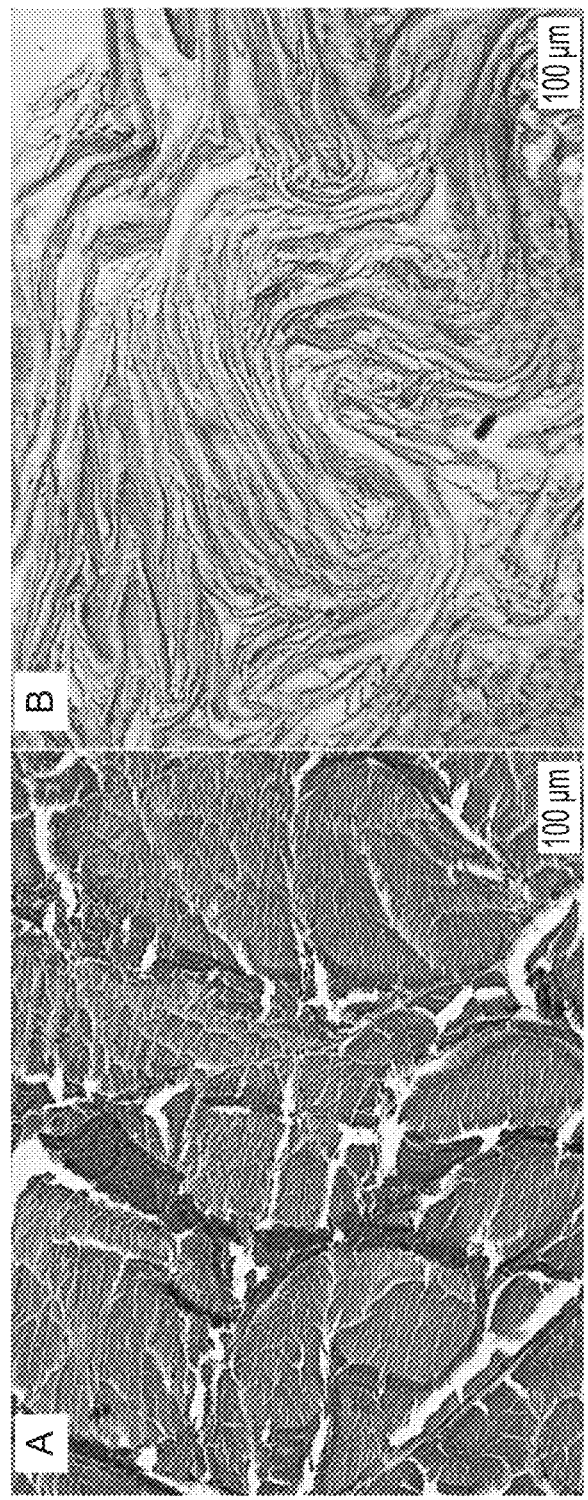
FIG. 11 provides images of hematoxylin & eosin (H&E) stained sections of healthy and tendinopathic tendon tissue, according to an example of the present disclosure.

FIG. 11 illustrates representative images of healthy and tendinopathic tendon tissue. The left image (A) of FIG. 11 displays an H&E stained cross-section of healthy tendon tissue at 10× magnification. As can be observed, the healthy tendon tissue has collagen fibers that are organized in tightly packed fiber bundles. The right image (B) of FIG. 11 displays an H&E stained cross-section of tendinopathic tendon tissue at 10× magnification. As can be observed, the tendinopathic tendon tissue has collagen fibers that are loosely organized and less compact, as evidenced by the increased space (light-colored areas) between fibers, and the numerous fiber shapes and orientations.

Tendon samples for the study comprised harvested bovine extensor tendons from the ankle of the donor animal. The tendons were chemically stabilized using Dulbecco's Modified Eagle Medium/Nutrient Mixture F-12 (DMEM/F12 50:50) mammalian cell culture. To prevent infection of the tissue, an antibiotic-antimycotic solution was incorporated into the stabilization solution. The tendon samples were stabilized at 37° C. and 5% $CO_2$ for four days.

Differences between healthy and tendinopathic tendon tissue can also be observed with ultrasound imaging. Healthy tendon and presents as uniform, white regions in an ultrasound image. Tendinopathic tendon tissue presents as hypoechoic, or darker than normal, regions in an ultrasound image. To evaluate the tendons after stabilization, the samples were prepared for ultrasound imaging. Each tendon sample was placed into a container with a 6 cm thick layer of 0.4% agarose gel. The tendon samples were then submerged in 0.9% saline. Ultrasound images were taken using a VEVO 3100 imaging system from Fujifilm Visualsonics (Toronto, Canada). Ultrasound images were captured along the length of the tendon samples at 0.08 mm intervals. A 3D model of each tendon sample was created from ultrasound slices using Fujifilm Visualsonics' software, Vevo Lab.

Next, to generate tendinopathic tissue, a 0.05 ml volume of 10 mg/ml Collagenase type I solution was injected into the center of a group of tendon samples. The Collagenase type I solution was mixed with 10% Trypan Blue to enhance visualization of the injectate. Simultaneously, a control group of tendon samples was injected with 0.05 ml of phosphate-buffered saline (PBS). Both groups of tendon samples were incubated for 24 hours in the same DMEM/F12 50:50, antibiotic-antimycotic solution as previously described.

After the 24 hour incubation period, the tendons were imaged using ultrasound a second time. Tendinopathic tissue was defined as a continuous hypoechoic (dark) region within the tendon cross-section, equal to or longer than 0.4 mm along the length of the tendon. To quantify the degree of tendinopathy within a given tendon, 3D imaging software was used to determine the volume fraction of tendinopathic tissue within the tendon. To calculate this value, the cumulative volume of tendinopathic tissue was divided by the volume of the entire tendon.

To determine the effect of Collagenase I and PBS injections on the tendon samples, volume fractions of tendinopathic tissue within the tendon samples were calculated before and after injections. Across 18 samples, pre-injection volume fractions averaged 0.066%. For the tendon samples injected with Collagenase I, after the 24 hour incubation period, the average volume fraction of tendinopathic tissue was 8.7%. For the control, PBS tendon sample, post-injection volume fractions averaged 0.056%.

While the mean volume fraction of the Collagenase I tendon samples were statistically different after injection, a t-test was conducted to determine if the mean volume fractions of the control, PBS tendon samples were statistically different after injection. In other words, the t-test sought to determine if PBS injections had a statistically significant effect on the volume of tendinopathic tissue within the tendon samples. The t-test yielded a p-value of 0.88, indicating that there was no statistically significant difference found between the means of the two control groups of tendon samples. This analysis indicated that PBS-injections did not increase the degree of tendinopathy within the control samples in a statistically significant way.

After the volume fractions were calculated post-incubation, the tendon samples were treated using the disclosed device. As described above, tissue samples were secured to a container on a layer of 0.4% agarose gel, submerged in 0.9% saline. To perform tissue treatment, the distal end of the disclosed device was positioned at the middle of the tendon sample, and the device was powered-on. Three tendinopathic and three control tendon samples were treated at power settings 5-10. The tendon samples were treated for two minutes. In the event that the evacuation aperture of the disclosed device became clogged, preventing evacuation of removing tissue from the treatment site, the timer was stopped. After the obstruction was cleared and the system purged, tissue removal and the timing of the procedure resumed.

After treatment, ultrasound imaging was performed a third and final time to quantify the volume fraction of tendinopathic tissue in the tendon samples. FIG. 12 illustrates a table containing average volume fractions of tendinopathic tissue within the Collagenase I-injected tendon samples, before and after treatment. As previously noted, three tendon samples were tested at each power setting. The tendinopathic tissue volume fractions, averaged across all power settings, decreased by approximately tenfold, dropping from 8.7% to 0.8% after treatment.

The data in FIG. 12 supports that the disclosed device can be used to dramatically reduce the volume fraction of tendinopathic tissue within Collagenase I-injected tendon samples, representative of tendinopathic tendons. This finding demonstrates that the disclosed device can be used to successfully remove tendinopathic tissue from healthy tendons in clinical applications.

FIG. 13 illustrates a table containing average volume fractions of control, PBS-injected tendon samples, before and after treatment. As before, three tendon samples were tested at each power setting. The tendinopathic tissue volume fractions, averaged across all power settings, increased from 0.06% before treatment to 0.30% after treatment. The data in FIG. 13 implies that the use of the disclosed device on healthy tendon tissue may induce minor tissue disruption, although quite minimally in comparison to the total tendon volume. However, unlike the control, PBS-injected tendons of this study, patients who would undergo treatment using the disclosed device would not possess tendons subjected to any form of fluid injection or fiber disruption. Thus, it is important to note that the control tendon data in FIG. 13 might not be entirely representative of treatment characteristics of healthy tendons within a patient.

Figure 14:
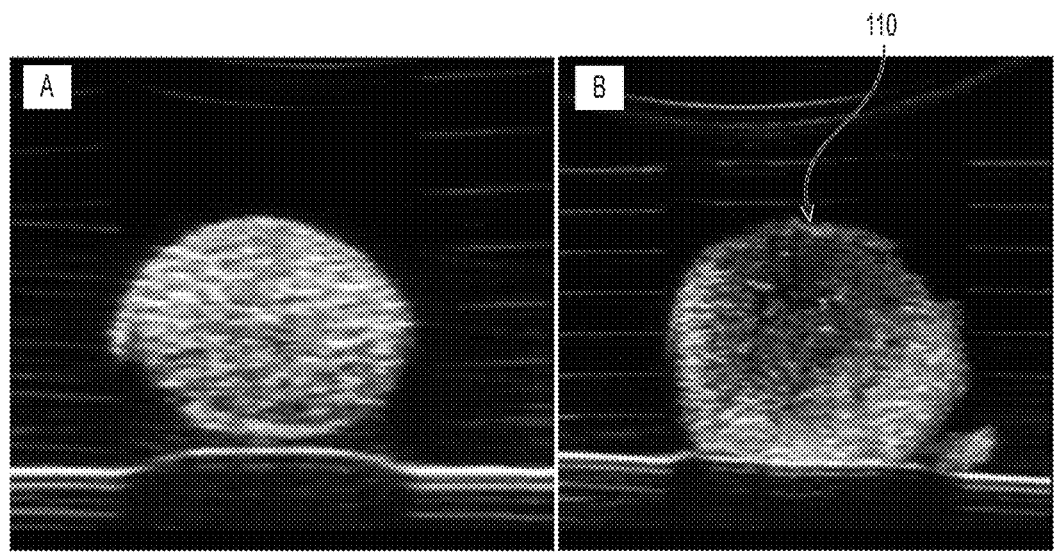
FIG. 14 provides ultrasound images of healthy and tendinopathic tendon tissue, according to an example of the present disclosure.

Ultrasound images from tendon sample are illustrated in FIG. 14. The left image (A) of FIG. 14 illustrates an ultrasound image of healthy tendon tissue from a sample used in this study. Notably, the healthy tendon appears as a solid, white sphere in the ultrasound image. The right image (B) of FIG. 14 illustrates tendinopathic tendon tissue within a sample form this study. The tendinopathic portion of the tendon presented as the dark, hypoechoic region 90, which takes up a significant portion of the tendon cross-sectional area. The white, crescent-shaped region of the right image (B) is representative of the remaining, healthy tendon tissue.

Histological analysis was performed on Collagenase I and PBS-injected tendon samples before and after treatment using the disclosed device. To generate histological images, all tendon samples were fixed in 10% Zinc Formalin for five days. In order to be embedded for histology, 2-3 mm thick cross-sections were cut from the middle of representative tendon samples. Approximately 6-8 µm thick slices of each tendon sample were created using a microtome, stained with Hematoxylin and Eosin (i.e. H&E), and imaged under an inverted light microscope.

Figure 15:
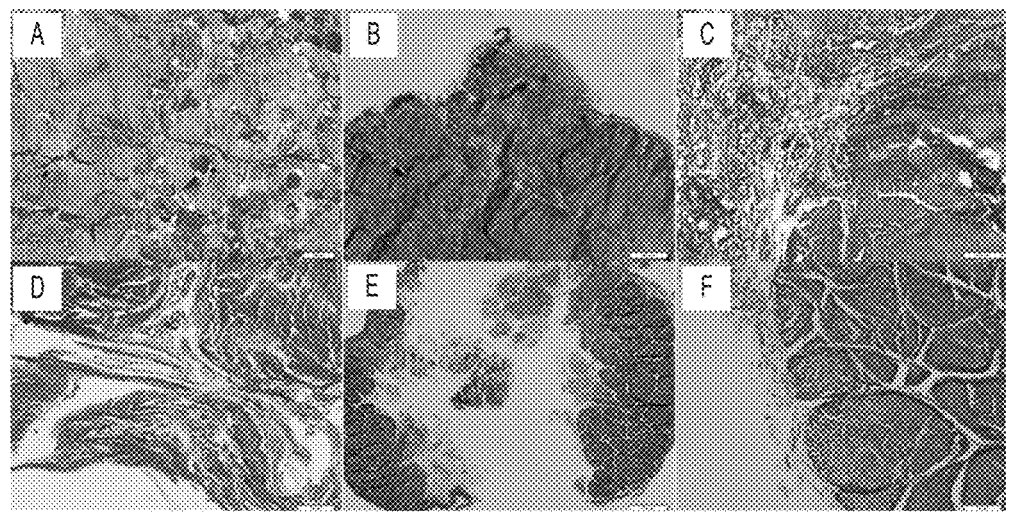
FIG. 15 provides images of H&E stained tendon from control and tendinopathic samples before and after treatment using the disclosed device, according to an example of the present disclosure.

FIG. 15 illustrates images of H&E stained tendon samples. The top row of images of FIG. 15 (A-C) illustrate cross-sections of control, PBS-injected tendon. Specifically, the top left image (A) illustrates a cross-section of control, PBS-injected tendon at 10× magnification before treatment. The top left image (A) illustrates a tendon with collagen fibers that are organized in tightly packed bundles with little, if any, void space between fibers or fiber bundles.

The top middle image (B) of FIG. 15 illustrates a cross-section of control, PBS-injected tendon treated with the disclosed device at 2× magnification. The top right image (C) illustrates a cross-section of control, PBS-injected tendon treated with the disclosed device at 10× magnification. Note that treatment of control, PBS-injected tendon samples using the disclosed device only slightly disrupts the organization and continuity of collagen fibers. Further, this disruption can only be clearly seen at 10× magnification.

The bottom row of images of FIG. 15 (D-F) illustrate images of H&E stained, Collagenase I-injected, tendinopathic tendon samples. Specifically, the bottom left image (D) illustrates a cross-section of tendinopathic tissue at 10× magnification before treatment. As is characteristic of tendinopathy, the collagen fibers in the bottom left image (D) are disorganized and more loosely bundled than healthy, control tissue. Also, there is more void space between collagen fibers and fiber bundles.

The bottom middle image (E) of FIG. 15 illustrates a cross-section of tendinopathic tissue treated with the disclosed device at 2× magnification. The bottom right image (F) illustrates a cross-section of tendinopathic tissue treated with the disclosed device at 10× magnification. As displayed in the bottom middle (E) and bottom right (F) images of FIG. 15, and as corroborated by the volume fraction data in FIG. 12, application of the disclosed device successfully removes the majority of the tendinopathic tissue from the remaining, healthy tendon. However, a very small amount of tendinopathic tissue remains, lining the treatment site. This small volume of remaining tendinopathic tissue is best seen in the bottom right (F) image of FIG. 15, where, abutting the left edge of the healthy tendon tissue, a relatively thin layer of tendinopathic tissue is visible.

Generally, the data from Example II provides further evidence that the disclosed device can be used to successfully treat patients who suffer from tendinopathy using minimally invasive techniques. Specifically, the disclosed device can remove the majority of the tendinopathic tissue from the affected tendon, leaving behind predominantly healthy tissue, thereby reducing inflammation and joint pain.

What is claimed is:

1. A method of treating a tendon using a surgical instrument comprising:

selecting a tendon; imaging the tendon to identify a region of said tendon that contains tendinopathic tissue; the surgical instrument comprising an insertion end comprising a first lumen and a second lumen each having a distal end comprising a closed terminal end portion and a proximal end; the first lumen extending along a longitudinal axis of the surgical instrument and including a nozzle formed in a side wall proximate the distal end of the first lumen and configured to enable a jet of fluid to exit the nozzle; and the second lumen including an aperture formed in a side wall proximate the distal end of the second lumen, the aperture abutting and opposite the nozzle of the first lumen, and configured to receive the jet of fluid exiting the nozzle, wherein the first lumen is directly connected to the second lumen from proximal end of the insertion end to the closed terminal end portions of the first lumen and the second lumen, the connection interrupted by the aperture; wherein the closed distal terminal end of the first lumen is located proximal the closed distal terminal end of the second lumen; inserting the distal ends of the surgical instrument proximate or within the tendinopathic tissue; powering the surgical instrument to create a jet of fluid and suction force proximate the distal ends of the surgical instrument, the jet of fluid forming a cutting and suction force at the aperture of the second lumen, the suction force selectively drawing tendinopathic tissue from a plurality of tissue types located in a surgical site into the aperture; cutting and suctioning at least a portion of said tendinopathic tissue; and evacuating at least a portion of said tendinopathic tissue through the aperture and an inner bore of the second lumen of the surgical device.

2. The method of claim 1, further comprising selecting a power level of the surgical device to adjust the cutting and suction force at the distal end of the surgical device.

3. The method of claim 1, wherein the tendinopathic tissue comprises pathologic tissues with a density of approximately 1,100 to 1,400 kg/m$^3$.

4. The method of claim 1, wherein the tendon having tendinopathy comprises a tendon having calcific tendinopathy.

5. The method of claim 1, wherein the jet of fluid comprises at least one of water or saline.

6. The method of claim 1, wherein the nozzle is 0.003-0.013 inches in width.

7. The method of claim 1, wherein the aperture is 0.055 0.11 inches in length.

8. The method of claim 1, wherein the aperture is 0.040 0.055 inches in depth.

9. The method of claim 1, wherein the first lumen and second lumen are disposed in a parallel configuration.

10. The method of claim 1, wherein the tendinopathic tissue is at least one of ligaments, hematomas, and debrided cartilage within and/or proximate the tendon.

11. The method of claim 1, wherein the tendon having tendinopathy is proximate a joint.

12. The method of claim 11, wherein the joint is one of an elbow, shoulder, knee, hip, ankle, or wrist joint.

* * * * *